(12) United States Patent
Pschierer

(10) Patent No.: US 12,076,425 B2
(45) Date of Patent: Sep. 3, 2024

(54) GLITTER AND ITS USE IN COSMETIC FORMULATIONS, COATING MATERIALS AND PLASTICS

(71) Applicant: Sigmund Lindner GmbH, Warmensteinach (DE)

(72) Inventor: Erwin Pschierer, Kastl (DE)

(73) Assignee: Sigmund Lindner GmbH, Warmensteinach (DE)

( * ) Notice: Subject to any disclaimer, the term of this patent is extended or adjusted under 35 U.S.C. 154(b) by 748 days.

(21) Appl. No.: 16/714,831

(22) Filed: Dec. 16, 2019

(65) Prior Publication Data

US 2020/0214951 A1 Jul. 9, 2020

(30) Foreign Application Priority Data

Dec. 14, 2018 (EP) ..................... 18212680

(51) Int. Cl.
| | | |
|---|---|---|
| *A61K 8/26* | (2006.01) | |
| *A61K 8/73* | (2006.01) | |
| *C23C 16/12* | (2006.01) | |
| *C23C 16/442* | (2006.01) | |

(52) U.S. Cl.
CPC ............... *A61K 8/26* (2013.01); *A61K 8/731* (2013.01); *C23C 16/12* (2013.01); *A61K 2800/10* (2013.01); *A61K 2800/42* (2013.01); *A61K 2800/621* (2013.01); *A61K 2800/652* (2013.01); *C23C 16/442* (2013.01)

(58) Field of Classification Search
CPC .................................. A61K 8/26; A61K 8/731
See application file for complete search history.

(56) References Cited

U.S. PATENT DOCUMENTS

2012/0040147 A1 2/2012 Komatsu et al.

FOREIGN PATENT DOCUMENTS

| EP | 494077 A1 * | 7/1992 | ............. B32B 29/06 |
|---|---|---|---|
| EP | 2418089 | 2/2012 | |
| EP | 2918630 | 9/2015 | |
| EP | 3106490 | 12/2016 | |
| JP | H05014200 U * | 2/1993 | |
| JP | H0620241 U * | 3/1994 | |
| JP | 2003026707 A * | 1/2003 | |

OTHER PUBLICATIONS

Tsai et al.,"Antibacterial cellulose paper made with silver-coated gold nanoparticles", Scientific Reports 7, Article No. 3155, 2017.*
Fenn et al. ("History of Roll-to-Roll Vacuum Coating", Society of Vacuum Coaters, 2007, 50th Annual Tech Conf Proceedings, 762-766).*
Europaeischer Recherchenbericht und die Stellungnahme zur Europaeischen Recherche [European Search Report and the European Search Opinion] Dated Apr. 2, 2020 From the European Patent Office Re. Application No. 19215065.4. (12 Pages).
Mitteilung Gemaess Artikel 94(3) EPUE [Communication Pursuant to Article 94(3) EPC] Dated Jan. 13, 2021 From the European Patent Office Re. Application No. 19215065.4. (7 Pages).
Mitteilung Gemäß Artikel 94(3) EPÜ [Communication Pursuant to Article 94(3) EPC] Dated Nov. 25, 2021 From the European Patent Office Re. Application No. 19215065.4. (6 Pages).
Europaeischer Recherchenbericht und die Stellungnahme zur Europaeischen Recherche [European Search Report and the European Search Opinion] Dated May 6, 2019 From the European Patent Office Re. Application No. 18212680.5. (11 Pages).
Bio Glitter "Bioglitter—Biodegradable in the Natural Environment", Bio Glitter, XP002789831, Retrieved From the Internet, 7 P., Jun. 28, 2018.
Bio Glitter "What Is Glitter and What Makes Bioglitter® Special?", Bio Glitter, Retrieved From the Internet, 3 P., Jun. 28, 2018.
Material District "BioGlitz Biodegradable Glitter to Reduce Microplastics", Material District, XP002789832, 2 P., Apr. 13, 2018.
Notification of Office Action and Search Report Dated Jan. 30, 2022 From the State Intellectual Property Office of the People's Republic of China Re. Application No. 201911292374.4 and Its Translation of Office Action Into English. (15 Pages).
Bioglitter, Bioglitter Biodegradable in the Natural Environment and What is Glitter and What Makes Bioglitter Special?, 7 pages, Jun. 28, 2018, retrieved from the internet Mar. 19, 2019, https://www.discoverbioglitter.com/hrf_faq/is-bioglitter-certified-to-compostability-standards-copy/ and https://www.discoverbioglitter.com/faqs.†

\* cited by examiner
† cited by third party

*Primary Examiner* — Gina C Justice

(57) ABSTRACT

The present invention relates to biodegradable glitters with enhanced solvent resistance and enhanced temperature stability, and also to the use thereof in cosmetic formulations, coating materials, and plastics; the glitters comprise a foil which comprises cellulose.

9 Claims, 5 Drawing Sheets

GLITTER AND ITS USE IN COSMETIC FORMULATIONS, COATING MATERIALS AND PLASTICS

RELATED APPLICATIONS

This application claims the benefit of priority of European Patent Application No. 18212680.5 filed on Dec. 14, 2018, the contents of which are incorporated herein by reference in their entirety.

FIELD AND BACKGROUND OF THE INVENTION

The present invention relates to a glitter comprising a foil which comprises cellulose, to its use in cosmetic products, coating materials (e.g., paints, varnishes, and printing inks), and plastics, and also to cosmetic products, coating materials, and plastics which comprise the glitter.

Glitters are much employed for producing a sparkling surface effect, and have a variety of uses, particularly in cosmetic articles, paints, varnishes, printing inks, and plastics. Such glitters are usually produced using foils or films of plastic, which by means of a cutting operation are cut into individual particles of comparably small size. At present it is primarily films of polyethylene terephthalate that are used for producing glitter. Used to a lesser extent are films composed of biodegradable films such as polylactose or cellulose acetate, for example, for producing glitter. Foils used for producing glitter are mostly coated with aluminum, so giving rise to a reflecting surface and allowing a pronounced sparkle effect to be produced.

One example of a method for producing such glitters is disclosed in DE 102010001971 A1. Disclosed herein are glitters which are coated from all sides.

From an environmental standpoint it is desirable to produce glitters from biodegradable materials. Known biodegradable foil materials, such as polylactose and cellulose acetate, for example, which are suitable for producing biodegradable glitter, are nevertheless not suitable, owing to a lack of solvent resistance, for certain applications, such as nail varnish, for example. Furthermore, these biodegradable glitters have lower temperature stability than glitters based on polyethylene terephthalate.

Cellulose, having a high degradation rate under various conditions (e.g., composting and fresh water), offers very good preconditions for the production of biodegradable glitters.

Under the name Bioglitter Sparkle, there are glitters on the market that include regenerated cellulose coated with further polymers. These glitters are less solvent-resistant than polyethylene terephthalate and have a lower temperature stability than polyethylene terephthalate-based glitters.

There are, furthermore, metallized foils known that consist partly of cellulose and are additionally coated with a polymer; the metallization is located externally on the coating. These foils are on the market, for example under the brand name Natureflex NM (Futamura Chemical Co, Ltd.), and these foils are usually coated with barrier layers (e.g., https://www(dot)transcendia(dot)com/sites/default/files/datasheet_download/NM-F_datasheet.pdf).

WO2012/137014A1 discloses coated biodegradable films. The biodegradable polymers which are used for the coating are wholly or partly soluble in the usual solvents such as esters and ketones, for example. The lack of resistance is manifested, for example, in the form of loss of gloss, deformation of the particles, and swelling or dissolution of the foil. In the case of foils disclosed therein that are coated with a metal, the metal layer may detach wholly or partly from the foil.

There is a need for glitters which are biodegradable and possess performance properties comparable with those of the known, polyethylene terephthalate-based glitters. In particular there is a desire for long-term resistance to solvent. A further desire is for a very high temperature stability.

The object on which the invention is based, therefore, is that of providing biodegradable glitters which exhibit enhanced resistance towards solvents. It is also an object of the invention to provide biodegradable glitters which feature better temperature stability and, on the basis of their high compatibility, can be used in cosmetic products. It is an object of the invention, moreover, to provide biodegradable glitters which, on account of the solvent resistance and temperature stability, can be used in coating materials and plastics.

SUMMARY OF THE INVENTION

Biodegradable glitters have to date been produced primarily using foils based on polylactose or cellulose acetate. There are also glitters known which comprise regenerated cellulose and have a coating of further polymers. It has emerged, surprisingly, that the object of the invention, namely glitters with enhanced solvent resistance, can be achieved by producing glitter using foils based on cellulose, the cellulose being coated directly with a metal or at least not coated with further polymers.

The present invention accordingly relates to glitters comprising a foil based on cellulose, wherein the glitter is coated with a metal, preferably aluminum, and wherein the coating of the metal takes place directly on the foil which comprises cellulose, or wherein the cellulose is not directly coated with a polymer layer. The invention further relates to the use of the glitter in cosmetic formulations, coating materials, and plastics, and also to cosmetic formulations, coating materials, and plastics comprising the glitters.

In a first aspect, the present invention is directed to glitter comprising a foil which comprises cellulose, wherein the glitter is coated with a metal, preferably aluminum, and wherein the coating of the metal takes place directly on the foil which comprises cellulose.

A second aspect relates to a glitter comprising a foil which comprises cellulose, wherein the cellulose is not coated directly with a polymer layer.

Additionally disclosed are the use of the glitters of the invention in cosmetic products, and also cosmetic products comprising the glitters of the invention.

Further disclosed are the use of the glitters of the invention in coating materials, and coating materials comprising the glitters of the invention. Disclosed, furthermore, are the use of the glitters of the invention in plastics, and also plastics comprising the glitters of the invention.

Further preferred refinements of the present invention will become apparent from the dependent claims and from the detailed description that follows of the invention.

BRIEF DESCRIPTION OF THE SEVERAL VIEWS OF THE DRAWINGS

The appended drawings are intended to illustrate embodiments of the present invention and to impart a further understanding thereof. In connection with the description, they serve to explain concepts and principles of the invention. Other embodiments and many of the stated advantages are apparent in relation to the drawings. The elements in the drawings are not necessarily shown to scale relative to one another. Elements, features, and components which are the same, the same in function, and the same in effect are each provided with the same reference symbols in the figures of the drawings, unless otherwise stated.

DESCRIPTION OF SPECIFIC EMBODIMENTS OF THE INVENTION

Definitions

Figure 1:
FIGS. 1, 2, 3, 4 and 5 show glitters of the invention schematically.

Unless otherwise defined, technical and scientific expressions that are used herein have the same meaning as commonly understood by a person skilled in the field of art of the invention.

Quantitative details in the context of the present invention relate to wt %, unless otherwise indicated or evident from the context. In the foil which comprises cellulose, the wt % fractions add up to 100 wt %.

Glitters are small particles having a wide variety of shapes. In particular they have a size—for example, a maximum diameter in a principal extent direction of the particle—of 0.02 mm to 7.0 mm, preferably 0.050 mm to 6.0 mm, for example 0.06 mm to 2.0 mm, e.g., 0.1 mm to 0.5 mm, for example from 100 μm to 400 μm. In terms of shape, the glitter particles are not subject to particular restriction, and may take the form, for example, of platelets, needles, cuboids, etc., or may have been punched into defined shapes, examples being hexagons, squares, circles, ovals, stars, etc. According to certain embodiments, the glitters have a flat configuration, in the form, for example, of platelets with any of a very wide variety of different shapes, including, for example, hexagonal, rectangular, square, star-shaped, round, oval, etc., and the thickness of the platelets in this case may preferably be between 4 μm and 50 μm, for example between 5 μm and 45 μm, e.g., between 10 μm and 35 μm, by way of example between 14 μm and 23 μm, and/or the size—for example, a maximum diameter in a principal extent direction of the glitters—may be from 0.02 mm to 7.0 mm, preferably 0.050 mm to 6.0 mm, for example 0.06 mm to 2.0 mm, e.g., 0.1 mm to 0.5 mm.

In a first aspect the present invention relates to glitter comprising a foil which comprises cellulose, wherein the glitter is coated with a metal, preferably aluminum, the coating of the metal taking place directly on the foil which comprises cellulose.

In a second aspect, a glitter is disclosed comprising a foil which comprises cellulose, wherein the cellulose is not coated directly with a polymer layer.

In particular the polymer layer here is a layer which influences technical properties, especially a layer for enhancing the lubricity, a barrier layer and/or a layer for promoting adhesion, where corresponding layers may be produced by means of corresponding polymer materials which are known to a person skilled in the art. The polymer layer here is preferably a layer which consists substantially of at least one polymer and/or copolymer and/or mixtures thereof or consists of a polymer and/or copolymer and/or mixtures thereof. In this embodiment, however, the polymer layer here is not a varnish layer. In contrast to the polymer layer, in the context of the present invention, a varnish layer serves for coloring and in accordance with certain embodiments, accordingly, comprises at least one pigment and/or a dye, there being no particular restriction on the pigment and/or the dye, although they are not polymeric.

The observations below relate to the first and second aspects of the present invention, unless otherwise evident or indicated to the contrary.

The invention imposes no particular restriction on the cellulose. For example, the foil may comprise cellulose and/or regenerated cellulose and/or mixtures thereof. Other designations for cellulose-based foils are cellophane, cellulose hydrate or glassine. According to certain embodiments, the cellulose is not regenerated cellulose.

The expression "modified cellulose" embraces derivatives of cellulose, these being compounds which can be prepared from cellulose, such as, for example, cellulose esters, e.g., cellulose acetate, cellulose acetate butyrate, cellulose acetate propionate; cellulose nitrate; cellulose ethers, e.g., methylcellulose, ethylcellulose, hydroxyethylcellulose, hydroxypropylcellulose, carboxymethylcellulose. The expression "regenerated cellulose" relates to cellulose which by comparison with the natural cellulose possesses an altered crystal lattice, with the high-molecular structure—consisting of glucose units—remaining unaltered. Regenerated cellulose can be produced, for example, from natural cellulose by swelling and/or dissolving operations.

According to certain embodiments, the foil comprises at least 60 wt % of cellulose and/or regenerated cellulose and/or mixtures thereof, preferably more than 60 wt %, more preferably more than 70 wt %, preferably more than 75 wt %, preferably 80 wt % or more, more preferably still more than 80 wt %, and especially preferably more than 90 wt %, for example more than 95 wt % or indeed more than 99 wt %, based on the weight of the foil.

The foil consists for example of 80 wt % of cellulose and/or regenerated cellulose—for example, regenerated cellulose.

According to certain embodiments, the foil consists substantially of cellulose and/or regenerated cellulose and/or mixtures thereof or indeed consists of cellulose and/or regenerated cellulose and/or mixtures thereof, aside from unavoidable impurities.

In addition, however, there may also be further adjuvants and/or one or more further polymers such as, for example, modified cellulose, starch, polylactic acid (PLA) etc., present in the foil, in an amount of up to 40 wt %, preferably less than 40 wt %, more preferably less than 30 wt %, more preferably still less than 20 wt %, and especially preferably less than 10 wt %, for example less than 5 wt %, or indeed less than 1 wt %, and are not subject to particular restriction.

For example, the foil may comprise as adjuvant, according to certain embodiments, glycerol triacetate (triacetin), urea and/or glycerol. The mass fraction in this case may preferably be less than 40 wt %, more preferably less than 30 wt %, more preferably still less than 20 wt %, more preferably still less than 15 wt %, and especially preferably less than 10 wt %, for example less than 5 wt %, or indeed less than 1 wt %, based on the weight of the foil. The foil may also contain no adjuvants. There could for example also be mixtures of two or more of the stated adjuvants present, examples being glycerol and urea, for example in amounts of 8 to 14 wt % of glycerol and 1 to 5 wt % of urea, e.g., in amounts of 10 to 12, for example 11, wt % of glycerol and 2 to 4, e.g., 3, wt % of urea.

Alternatively or additionally, the foil, according to certain embodiments, may comprise additives, which may act, for example, as antiblocking agents and/or lubricity assistants.

These antiblocking and/or lubricity assistants are not subject to particular restriction and may comprise, for example, amorphous silicas, crystalline silicas, fatty acid amides and/or talc. The amount in which such antiblocking agents and/or lubricity assistants are added may, according to certain embodiments, be 0-2.5 wt %, preferably 0-1.5 wt %, more preferably 0-1 wt %, based on the weight of the foil. The foil may also comprise solvents such as water, for example in an amount of less than 20 wt %, preferably less than 10 wt %, more preferably less than 8 wt %, more preferably still less than 7 wt %. According to certain embodiments, the foil may comprise solvents such as water in an amount of not less than 1 wt %, preferably at least not less than 3 wt %, more preferably still at least 5 wt %, for example 6 wt %.

Alternatively or additionally, the foil, according to certain embodiments, may comprise pigments and/or fillers, which may influence, for example, the color or the mechanical properties. These pigments and/or fillers are not subject to particular restriction and may comprise, for example, calcium carbonate, magnesium carbonate, barium sulfate and/or mica. The mass fraction In this case may preferably be less than 40 wt %, more preferably less than 30 wt %, more preferably still less than 20 wt %, and especially preferably less than 10 wt %, for example less than 5 wt %, or indeed less than 1 wt %, based on the weight of the foil. The foil may also contain no pigments and/or fillers.

In the first aspect of the present invention, the foil is coated with a metal, preferably aluminum, silver, gold and/or copper, more preferably aluminum. The coating in this case may, according to certain embodiments, take place on one side, on two opposite sides, on the entire foil, or otherwise. The metal-coated foils preferably have an optical density of more than 1.0, more preferably of more than 1.5, more preferably still more than 2.0, more preferably still more than 2.5. The optical density here may be measured using, for example, a densitometer.

According to certain embodiments, the glitter consists of the foil which comprises cellulose, and the glitter is coated with a metal, preferably aluminum, and the coating of the metal takes place directly on the foil which comprises cellulose.

The foil and/or a metal layer, an aluminum layer for example, of the first aspect may according to certain embodiments be coated with a coating based on a polysaccharide, preferably a linear polysaccharide, more preferably based on pullulan and/or on cellulose or modified cellulose, more preferably still based on cellulose nitrate, cellulose acetate butyrate, cellulose acetate propionate and/or cellulose acetate and/or pullulan, and/or based on polyvinyl alcohol and/or shellac and/or polyurethane. Here as well the coating may be present on one side, two opposite sides, on the entire metal layer, aluminum layer for example, of the foil and of the metal layer, aluminum layer for example, or otherwise. Preference is given to a coating with pullulan and/or cellulose acetate. According to certain embodiments, the coating is on the foil and the metal layer.

In the coating the polysaccharide is not subject to particular restriction, but is preferably a linear polysaccharide, which is also not restricted. A coating based on a polysaccharide encompasses coatings with the polysaccharide and/or derivatives of the polysaccharide, which are not particularly restricted. A coating based on a linear polysaccharide encompasses coatings with the linear polysaccharide and/or derivatives of the linear polysaccharide, which are not particularly restricted. Coatings based on pullulan encompass, correspondingly, coatings with pullulan and/or derivatives thereof, which are not particularly restrictive. Coatings based on cellulose encompass coatings with cellulose and/or derivatives of cellulose, which are not particularly restrictive. Coatings based on modified cellulose encompass coatings with modified cellulose. Correspondingly, coatings based on cellulose nitrate, cellulose acetate butyrate, cellulose acetate propionate and/or cellulose acetate encompass coatings of cellulose nitrate, cellulose acetate butyrate, cellulose acetate propionate and/or cellulose acetate and/or derivatives thereof. Derivatives of the coatings encompass, for example, copolymers of the corresponding polymers and/or coatings in which further constituents are included, for example with less than 50, 40, 30, 20, 10 or 5 wt %, based on the coating. The further constituents may comprise those which are usually present in coatings. Preferably, however, the coating comprises substantially no—that is, less than 5, 4, 3, 2 or 1 wt %—or no further constituents.

According to certain embodiments, the glitter consists of the foil which comprises cellulose, wherein the glitter is coated with a metal, preferably aluminum, and wherein the coating of the metal takes place directly on the foil which comprises cellulose,
and wherein the foil which comprises cellulose, and/or the metal layer, preferably the foil which comprises cellulose and the metal layer,
is coated with a coating based on a polysaccharide, preferably a linear polysaccharide, more preferably based on pullulan and/or on cellulose or modified cellulose, more preferably still based on cellulose nitrate, cellulose acetate butyrate, cellulose acetate propionate and/or cellulose acetate and/or pullulan, and/or based on polyvinyl alcohol and/or shellac and/or polyurethane. Preference is given to a coating comprising pullulan and/or cellulose acetate. According to certain embodiments, the coating is on the foil and the metal layer.

In the coating as well there may be further constituents present in addition the stated materials, such as, for instance, pigments and/or dyes and/or solvents such as water.

Especially preferred are coatings based on cellulose or modified cellulose, preferably based on cellulose nitrate, cellulose acetate butyrate, cellulose acetate propionate and/or cellulose acetate, especially cellulose acetate, and/or based on pullulan.

Furthermore, the glitter of the invention may also comprise further color-imparting and/or effect-imparting layers, of the kind known to a person skilled in the art and which a person skilled in the art can suitably apply, from the gas phase or from liquid/solution, for example.

The glitter of the invention may for example be coated with a varnish layer. In this case there is no particular restriction on the varnish layer, which according to certain embodiments comprises at least one pigment and/or one dye, which are not particularly restricted, but preferably are not polymers.

According to certain embodiments, the foil of the glitters of the invention has a thickness of 5 µm or more, preferably of more than 10 µm, more preferably of more than 13 µm, and/or a thickness of 50 µm or less, for example less than 40 µm, preferably 36 µm or less.

According to certain embodiments, moreover, the foil may be transparent or substantially transparent, with a transmissivity or degree of transmission for light in the visible range from 380 to 780 nm of, for example, 70%, or 80%, or 90% or more. According to certain embodiments, therefore, the foil has a transmissivity for light in the wavelength range from 380 to 780 nm of at least 70%, preferably at least 80%, more preferably at least 90%. The transmissivity here may be determined in a suitable way, such as with a suitable optical spectrometer, for example.

The foil, according to further embodiments, may be colored or uncolored, but according to certain embodiments is uncolored. In certain embodiments, moreover, a color-imparting layer may be applied to the coating with metal, preferably aluminum, or to the foil and the metal coating, or to the foil in the second aspect.

According to certain embodiments, the foil in a glitter of the invention may also be produced with a hologram imprint, of the kind known for conventional glitter, being known, for example, from U.S. Pat. No. 5,810,957 or EP2163 381 A, both documents being referenced with regard to the hologram imprint. It is also possible, surprisingly, to realize the hologram imprint on the foil comprising cellulose. For production in this case, it is possible to use common methods, such as those known as soft embossing and hard embossing.

Below, the invention is explained in more detail, using exemplary embodiments of glitters of the invention (especially of the first aspect in FIGS. 2 to 5) which are shown in FIGS. 1 to 5. The figures here show, schematically, sectional views through glitters having a construction in accordance with the invention.

Glitters of the invention here comprise, for example, glitter particles having a size of 100 μm to 200 μm and a thickness of 19 μm to 30 μm, but are not restricted to these. According to a first exemplary embodiment of the second aspect, which is shown in FIG. 1, transparent particles 1 consisting substantially of cellulose, as the foil of the glitters of the invention, may be obtained by cutting a cellulose foil. In this case there is no further polymer layer present on the cellulose foil.

Figure 2:

According to an embodiment of the first aspect which is shown in FIG. 2, the particles 1 consisting substantially of cellulose may be coated on one side with a metal layer, an aluminum layer 2 for example. A coating of aluminum may in this case be applied preferably by vapor deposition under reduced pressure.

Figure 3:

According to a further embodiment of the first aspect, which is shown in FIG. 3, the particles 1 consisting substantially of cellulose may be coated on two opposite sides with a metal layer, an aluminum layer 2 for example. A coating of aluminum here may be applied preferably by vapor deposition under reduced pressure.

Figure 4:
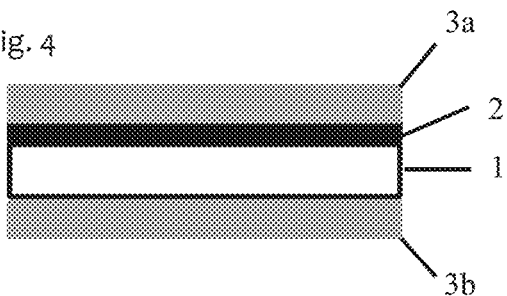

Furthermore, the particles 1 of the first aspect, coated on one side with aluminum 2 and consisting substantially of cellulose, may in a further embodiment, as shown in FIG. 4, be additionally coated evenly on two opposite sides with layers 3a, 3b of, for example, cellulose acetate.

Figure 5:

Alternatively the particles 1 of the first aspect, coated on one side with aluminum 2 and consisting substantially of cellulose, may in a further embodiment, as shown in FIG. 5, be coated evenly on all sides with a layer 4 of, for example, cellulose acetate.

In FIGS. 1 to 5, the foil consisting substantially of cellulose may, according to alternative refinements, also be colored. In FIGS. 4 to 5, moreover, the layers of cellulose acetate 3a, 3b and/or 4 on the particles consisting substantially of cellulose may, according to alternative refinements, also be colored.

There are no particular restrictions on the process for producing the glitters of the invention. A foil, especially comprising cellulose, may in this case be suitably cut into particles of suitable size and optionally coated in a usual way with metal, polymer, etc. In this context, a low tensile strength and low lubricity, especially of cellulose foils, for example, may have effects on the processing properties during glitter production. During glitter production the foils are typically processed "from roll". In that case, the tensile forces acting on the foils in the processing machines (e.g., foil coating and/or glitter cutting machine) are usually high. In the course of processing, therefore, it is necessary to minimize the tensile forces that occur, so as to prevent the foil breaking in the processing machines.

This may be achieved, for example, by a correspondingly designed web guidance system in the processing machines and by the corresponding design of the web-guiding transport rollers, in order to prevent excessive tensile forces on the foil.

There are no particular restrictions on the application of various coatings, which may for example take place from the gas phase and/or from solution.

A further aspect of the present invention is directed to the use of glitters of the invention in cosmetic products. There are no particular restrictions here on the cosmetic product. Cosmetic products here encompass, for example, pastes, salves, creams, emulsions, solutions, lipstick, lip gloss, mascara, mousse, eyeshadow, eyeliner, powder, pressed powder, loose glitter powder, nail varnish, soaps, shampoo, sun protection compositions, lotions, aerosol sprays, etc., which may comprise the glitter in usual amounts in the formulations.

Disclosed, moreover, is a cosmetic product which comprises glitters of the invention. There are no particular restrictions here on the cosmetic product, which may for example be a paste, a salve, a cream, an emulsion, a solution, a lipstick, lip gloss, mascara, mousse, eyeshadow, eyeliner, powder, pressed powder, loose glitter powder, nail varnish, soap, shampoo, sun protection composition, a lotion, an aerosol spray, etc., where the glitter may be present in usual amounts in the cosmetic product, for example between 0.01 and 75 wt %, e.g., between 1 and 10 wt %, based on the cosmetic product, or indeed up to 100 wt % in the case of powder and loose glitter powder. The cosmetic products may additionally comprise the usual constituents, such as carriers, fillers, oils, waxes, fats, emulsifiers, antioxidants, film-formers, odorants and/or flavors, stabilizers, solvents, surfactants, preservatives, thickeners, rheological additives, dyes, vitamins, buffer substances, active cosmetic ingredients, skin-active substances, e.g., skincare substances, UV filters, etc., all of which are not subject to any particular restriction. The cosmetic products may for example be hydrophilic, hydrophobic and/or lipophilic. Corresponding constituents are known, for example, from DE 102005055576 A1, to which reference is made by way of example in respect of cosmetic formulations for producing cosmetic products.

Additionally disclosed is the use of the glitters of the invention in coating materials, as also in coating systems, preferably from the sector of varnishes, paints, printing inks, adhesives, and sealants, which here are not subject to any particular restriction and may comprise the glitters in customary amounts. A coating material in this context is a material in liquid, paste or else powder form which is applied to the full area or part of objects and is able to form a coat through chemical or physical processes. For the use in printing inks, for gravure printing or flexographic printing, for example, there are a multiplicity of printing inks and overprint varnishes that are suitable, as sold for example by the companies Marabu, Pröll, Hartmann, Siegwerk, Rotoflex, GSB-Wahl and/or Coates Screen. The coating materials may have a waterborne or solventborne construction.

The glitters of the invention are compatible with a multiplicity of typical formulations from the sectors of paints, varnishes, adhesives, and sealants.

Further disclosed is a coating material which comprises the glitter of the invention. The amount of the glitters in the coating material is not subject to any particular restriction here, and may encompass usual amounts, depending on the respective coating material. In coating materials the glitters of the invention are used for example in concentrations of 0.1 wt % to 70 wt %, preferably in concentrations of 0.5 wt % to 50 wt %, more preferably in concentrations of 0.5 wt % to 10 wt %, based on the coating material. The coating material may be for example a varnish, a paint, a printing ink, an adhesive and/or a sealant.

Disclosed, moreover, is the use of glitters of the invention in plastics, which may find use, for example, in decorative and/or household objects. There are no particular restrictions on the plastics here, and they encompass, for example, thermoplastics such as polystyrene, polypropylene, polyethylene, and/or acrylonitrile-butadiene-styrene copolymer, for example; thermosets such as unsaturated polyester resins, epoxy resins, and/or phenolic resins, for example; and/or elastomers such as butadiene rubber, for example.

Further disclosed are plastics which comprise the glitters of the invention. There are no particular restrictions on the plastics or on the amount of the glitters used therein, and these may comprise usual plastics and amounts. In plastics the glitters of the invention may be present, for example, in concentrations of 0.01 wt % to 50 wt %, preferably in concentrations of 0.05 wt % to 20 wt %, more preferably in concentrations of 0.5 wt % to 10 wt %, based on the plastics. The plastics in this case may be or comprise, for example, thermoplastics such as polystyrene, polypropylene, polyethylene, and/or acrylonitrile-butadiene-styrene copolymer, for example; thermosets such as unsaturated polyester resins, epoxy resins, and/or phenolic resins, for example; and/or elastomers such as butadiene rubber, for example.

The above embodiments, refinements, and developments may be combined with one another as desired, where such combination is rational. Further possible refinements, developments, and implementations of the invention also encompass combinations, not stated explicitly, of features of the invention that are described above or below with reference to the exemplary embodiments. In particular, the person skilled in the art will also add individual aspects as improvements or supplementations to the respective basic form of the present invention.

The invention is elucidated further in detail with reference to various examples thereof. The invention, however, is not restricted to these examples.

EXAMPLES

Example 1: Solvent Resistance of Glitter

Glitters of the invention in accordance with FIG. 2 were produced by coating a cellulose foil having a thickness of 14 µm to 30 µm with aluminum by direct vapor deposition on one side and then cutting to a size of 100 µm to 200 µm.

The composition of the cellulose foil is as follows:

80% cellulose (regenerated)

11% glycerol

6% water

3% urea

Coating with aluminum takes place by reduced-pressure vapor deposition, the coating having an optical density of 1.9-2.2.

Particle size and particle thickness were measured for selected exemplary glitter particles from example 1, by means of light microscopy (Zeiss Scope A1 with AxioCam MRc), giving the values reported in table 1.

TABLE 1

Measured values of particle thickness and particle size of glitter particles of example 1

|  | Particle thickness | Particle size |
|---|---|---|
| Measurement 1 | 22 µm | 200 µm |
| Measurement 2 | 22 µm | 209 µm |
| Measurement 3 | 23 µm | 208 µm |
| Measurement 4 | 21 µm | 205 µm |
| Measurement 5 | 22 µm | 206 µm |

The optical density (OD=−lg I/$I_o$ where $I_o$ is the intensity of the irradiated light) of selected exemplary glitter particles from example 1 was measured with a densitometer (Mcbeth TD904 red filter at 624 nm).

TABLE 2

Measured values of the optical density of glitter particles of example 1

|  | Optical density OD |
|---|---|
| Measurement 1 | 2.1 |
| Measurement 2 | 2.0 |
| Measurement 3 | 2.0 |
| Measurement 4 | 1.9 |
| Measurement 5 | 2.2 |

For comparison, glitters with foils of polylactic acid (PLA), cellulose acetate, Natureflex NM (single-sidedly metallized foil with a cellulose film coated with a coating, from Innovia Films) and polyethylene terephthalate (PET) were produced by corresponding methods with the same size and coating. Likewise used, as reference examples, were the "Bioglitter Sparkle Silver 008 (article number 8301/008H.FDA)" glitter from Ronald Britton, and the "GU CJC98AL-008H Cellulose Silver Zodiac 0.008 Hex" glitter from Meadowbrook Inventions, Inc.

With the various materials, the resistance to solvents was tested by introduction into pure ethyl acetate at 50° C. for 24 h. For this purpose, the glitters were placed into a sample bottle and overlayered with ethyl acetate, and their resistance was observed. The results are reported in table 3.

TABLE 3

Solvent resistance of the glitters in example 1

|  | Cellulose | Cellulose acetate | PLA | Natureflex NM | PET | Bioglitter Sparkle Silver 008 | Cellulose Silver Zodiac .008 hex |
|---|---|---|---|---|---|---|---|
| Ethyl acetate 24 h at 50° C. | No visible change | Loss of gloss | Swelling and dissolution of the foil | Loss of gloss and detachment of the metallization | No visible change | Loss of gloss and detachment of the metallization | Detachment of the metallization |

The solvent resistance of the cellulose-based glitter is comparable with the resistance of glitter based on polyethylene terephthalate. This provides evidence of the outstanding utility of cellulose foils in glitters of the invention in comparison to those of the prior art.

Example 2: Temperature Stability of Glitter

Glitters of the invention as per FIG. 3 were produced by coating a cellulose foil having a thickness of 23 µm to 35 µm with aluminum by vapor deposition on two opposite sides and then cutting to a size of 200 µm to 400 µm.

For comparison, glitters were produced with films of polylactic acid (PLA), cellulose acetate and polyethylene terephthalate (PET) by corresponding methods, with the same size and coating. Likewise, for comparison, the "Bioglitter Sparkle Silver 008" glitter from Ronald Britton was again used.

The temperature stability was tested with the various materials. For this purpose, the glitters were heated and inspected. The maximum temperature stability here, then, is the temperature up to which no change in the glitter can be found. Optical changes such as loss of gloss, for example, then occur at higher temperatures. The results are reported in table 4.

TABLE 4

Temperature stability of the glitters in example 2

|  | Cellulose | Cellulose acetate | PLA | PET | Bioglitter Sparkle Silver 008 |
|---|---|---|---|---|---|
| Maximum temperature stability in ° C. | 240° C. | 120° C. | 60° C. | 220° C. | 80° C. |

The temperature stability of the cellulose-based glitter exceeds the temperature stability of glitter based on polyethylene terephthalate, and of the other materials.

This provides evidence of the outstanding utility of cellulose foils in glitters of the invention in comparison to those of the prior art.

Example 3: Application Examples of Glitters of the Invention

In the formulation examples below, a comparative assessment is made in each case of a glitter of the invention (glitter example as per example 1) and a prior-art glitter (comparative glitter consisting of a polyethylene terephthalate film with Al coating with the same size from example 1).

These glitters were used to produce a variety of products from the sectors of cosmetics, varnishes, printing inks, and plastics, in a usual way, with the constituents/ingredients and fractions (wt % based on the products) according to the respective details in tables 5, 6 and 7.

Product 1: Nail Varnish

TABLE 5

Nail varnish composition

|  | Ingredient | % w/w |
|---|---|---|
| Phase A | Ethyl acetate | 31.0 |
|  | Butyl acetate | 23.0 |
|  | Nitrocellulose | 13.0 |
|  | Phthalic anhydride/trimellitic anhydride/glycol copolymer | 7.0 |
|  | Isopropanol | 5.0 |
|  | Dipropylene glycol dibenzoate | 5.0 |
|  | n-Butanol | 5.0 |
|  | Silica | 3.0 |
|  | Acetyltributylcitrate | 2.0 |
|  | Acrylate copolymer | 2.0 |
|  | Ethanol | 1.0 |
| Phase B | Glitter | 3.0 |
|  | Total | 100.0 |

Production:
1. Mix ingredients of phase A
2. Mix phase B into phase A

Shelf life testing: Storage of the glitter-containing nail varnish at 50° C. for 7 days.

The shelf life of the cellulose-based glitters is of a comparable quality to that of glitters based on polyethylene terephthalate. There is no detectable optical alteration of the cellulose-based glitters in the nail varnish during the storage period.

This demonstrates the outstanding utility of cellulose foils in glitters of the invention in comparison to those of the prior art.

Product 2: Baking Varnish

TABLE 6

Baking varnish composition

| Ingredient | % w/w |
|---|---|
| Setal 90173 SS-50, Allnex | 50.0 |
| Setamin US 138 BB-70, Allnex | 15.0 |
| Methoxypropyl acetate | 14.5 |
| Butyl acetate | 14.5 |
| CAB 381-0.5, Eastman | 5.0 |
| Glitter | 1.0 |
| Total | 100 |

Production:
Mix ingredients
Processing:
Apply varnish using wire doctor (100 μm) to aluminum panel. Leave to evaporate at room temperature for 20 minutes. Bake at 160° C. for 30 minutes.

The temperature stability of the cellulose-based glitters is of a comparable quality to that of glitters based on polyethylene terephthalate.

This demonstrates the outstanding utility of cellulose foils in glitters of the invention in comparison to those of the prior art.

Product 3: Printing Ink

TABLE 7

Printing ink composition

| Ingredient | % w/w |
|---|---|
| FlexiPrint MV extender varnish, Flint Group | 97.0 |
| Glitter | 3.0 |
| Total | 100.0 |

Production:
Mix ingredients
Processing:
Apply printing ink using wire doctor (20 μm) to aluminum panel. Leave to evaporate at room temperature for 5 minutes. Dry at 140° C. for 15 minutes.

Product 4: Plastic 1 kg of LLDPE (linear low-density polyethylene) is wetted evenly with 5 g of bonding agent in a tumble mixer. 10 g of glitter are added thereto and the mixture is mixed for 2 minutes, after which granules are produced on a twin screw extruder. These granules are processed under usual conditions on an injection molding machine to form stepped plaques having dimensions of 4×6 cm.

The glitter of the invention exhibits highly reflecting, punctiform sparkle effects in the plastic plaques.

Example 4: Temperature-Stable Glitters with Narrow Particle Size Distribution

A glitter of the invention in accordance with FIG. 3 was produced, having the following composition (wt %):
99.5% glassine 40 g/m²
0.5% aluminum
The composition of the glassine in wt % was as follows:
88.5% cellulose
6.5% water
2.5% calcium carbonate
2.5% magnesium carbonate The aluminum was coated directly onto the glassine by means of vapor deposition under reduced pressure.

The particle size and particle thickness were measured in example 4 by light microscopy, as in example 1. The results of the measurement are set out in table 8.

TABLE 8

Measured values of particle thickness and particle size of glitter particles of example 4

| | Particle thickness | Particle size |
|---|---|---|
| Measurement 1 | 30 μm | 371 μm |
| Measurement 2 | 31 μm | 387 μm |

TABLE 8-continued

Measured values of particle thickness and particle size of glitter particles of example 4

| | Particle thickness | Particle size |
|---|---|---|
| Measurement 3 | 30 μm | 389 μm |
| Measurement 4 | 30 μm | 382 μm |

Example 5: Solvent-Resistant Glitter with Pullulan Coating

The glitter from example 1 is given a colored coating by a fluidized bed method.

To accomplish this, 1.0 kg of glitter is placed into the reservoir of a fluidized bed unit (ProCell Lab System, Glatt) and fluidized with 80 m³/h. The incoming air temperature is 50° C. The color varnish, consisting of 25 g of pullulan (CAS 9057-02-7), 150 g of water, and 20 g of tartrazine yellow (CI 19140), is sprayed onto the glitter with a spray pressure of 1.6 bar over the course of 30 minutes.

The gold-colored glitter formed in this process corresponds to the schematic representation in FIG. 5.

Exemplary thickness measurements (measured as in example 1) produced the following values: 22 μm, 20 μm, 24 μm, 23 μm.

For the glitter produced, the solvent resistance ("bleeding") is analyzed as follows: 0.2 g of glitter is introduced in a test tube, overlayered with 3 ml of methyl ethyl ketone, and sealed with a stopper. After 1 minute, the test tube is shaken for 5 seconds and then stored at room temperature. The solvent resistance is assessed visually on the basis of the discoloration of the methyl ethyl ketone:
0: no discoloration=solvent-resistant
1: visible discoloration=not solvent-resistant The comparative glitter used was Bioglitter Sparkle Gold from Ronald Britton.

The results of the measurement are shown in table 9.

TABLE 9

Measured values of the solvent resistance in example 5:

| | After 5 minutes | After 30 minutes | After 5 hours | After 24 hours |
|---|---|---|---|---|
| Glitter of example 5 | 0 | 0 | 0 | 0 |
| Bioglitter Sparkle Gold, Ronald Britton | 1 | 1 | 1 | 1 |

Example 6: Glitter with Colored Coating

The glitter from example 1 is given a colored coating by a fluidized bed method.

To accomplish this, 1.0 kg of glitter is placed into the reservoir of a fluidized bed unit (ProCell Lab System, Glatt) and fluidized with 80 m³/h. The incoming air temperature is 50° C. The color varnish, consisting of 20 g of cellulose acetate, 15 g of yellow iron oxide, and 100 g of methyl ethyl ketone, is sprayed onto the glitter with a spray pressure of 1.6 bar over the course of 45 minutes.

The glitter formed in this process corresponds to the schematic representation in FIG. 5.

Comparative Example 1

Comparative tests were carried out with Bioglitter from Ronald Britton. The Bioglitter pure from Ronald Britton contains no aluminum coating and therefore differs from that of the present invention.

To investigate the layer construction, a Bioglitter Sparkle from Ronald Britton was analyzed by FT-IR and pyrolysis-GC/MS in order to study how the differences can be explained in solvent resistance and temperature stability between glitters of the invention and those from Ronald Britton.

The pyrolysis-GC/MS system used consists of Trace GC (Thermo Scientific) and DSQ (Thermo Scientific) with Pyrola 2000 (Pyrolabs).

Analysis Conditions:
- sample quantity: about 0.5 mg
- pyrolysis: 500° C./10 s/He
- GC: 2 min 100° C./15 K/min 6 280° C./25 min 280° C.
- column: Restec Q-Bond/1.5 ml/min He
- DSQ: EI+200° C.

Procedure:

Parts (about 0.2 mg) of the samples were taken or separated off, applied to the filament of the Pyrola 2000, and pyrolyzed at about 500° C./10 s. The pyrolysis products are swept directly with the gas stream onto the GC column and after separation are analyzed by mass spectrometry (total ion stream chromatogram).

The FTIR analysis was carried out by the ATR method:
Golden Gate Diamant ATR unit, FMIR unit
Wavenumbers: 4000 cm-1 to 600 cm-1
Resolution: 4 cm-1, number of scans: 16

Figure 6:
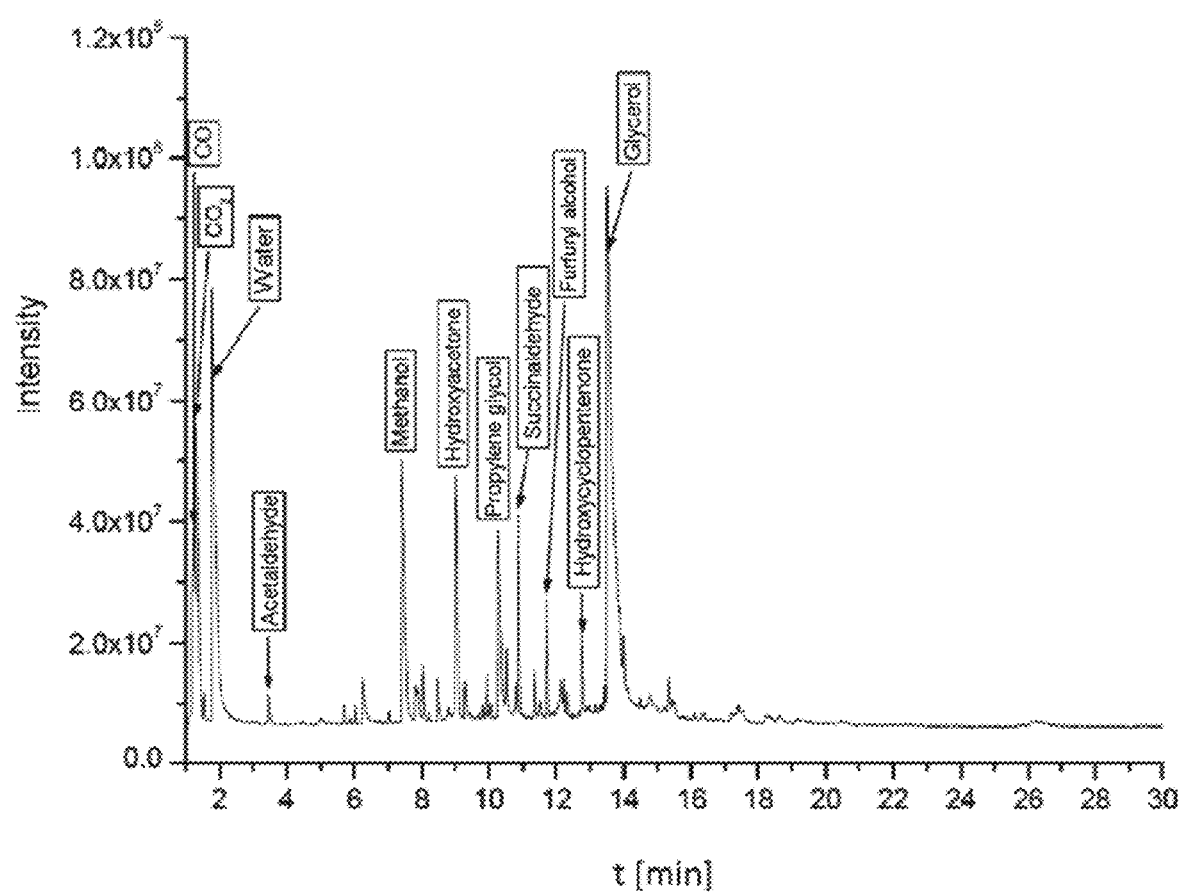
FIGS. 6, 7, 8 and 9 show measured values from GC-MS and FT-IR measurements of glitters or glitter foils of the invention and those of the prior art.
Figure 7:
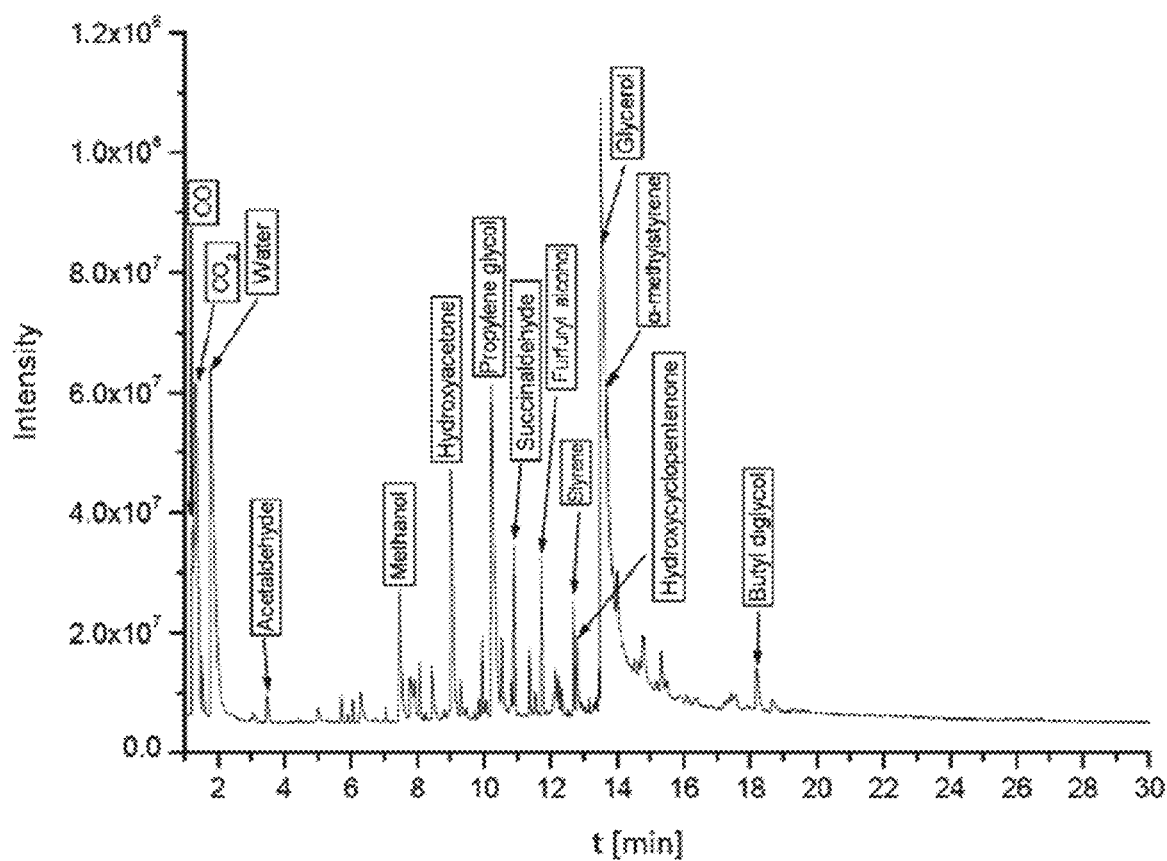

The analysis revealed that the Bioglitter Sparkle from Ronald Britton contains additional polymer layers. This is apparent from FIGS. 6 and 7 (pyrolysis-GC/MS) and 8 and 9 (FT-IR). FIGS. 6 and 7 here show the results of a pyrolysis-GC/MS at 500° C. for 10 s with a Restec Q-bond column. From the figures it is apparent that Bioglitter Sparkle in FIG. 7, in contrast to the glitter of the invention from example 1, shown in FIG. 6, additionally contains styrene, methylstyrene, and butyl diglycol. Styrene and methylstyrene suggest a styrene/acrylate coating, and butyl diglycol a polyester-based coating.

These results are consistent with the FTIR analysis of commercially available metallized cellulose foils (Futamura, Natureflex NM), as used as comparative foils in example 1.

Figure 8:
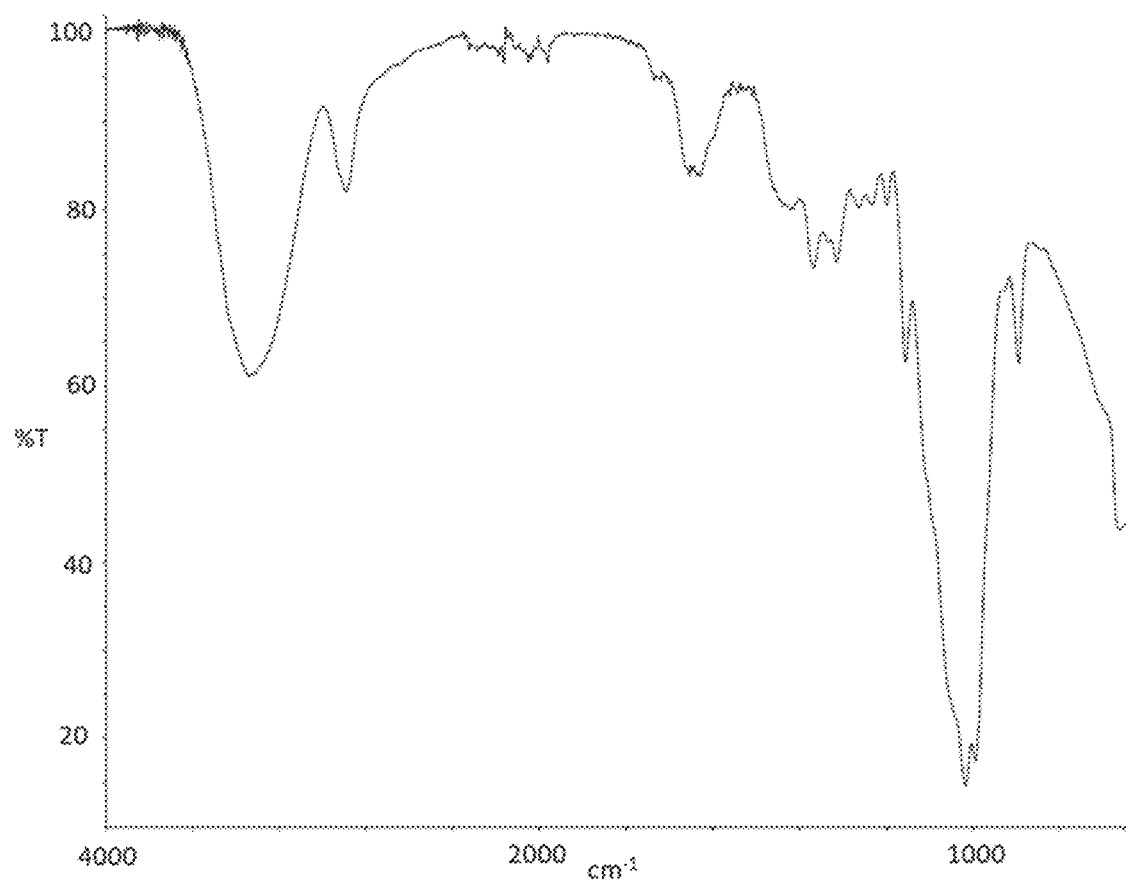
Figure 9:
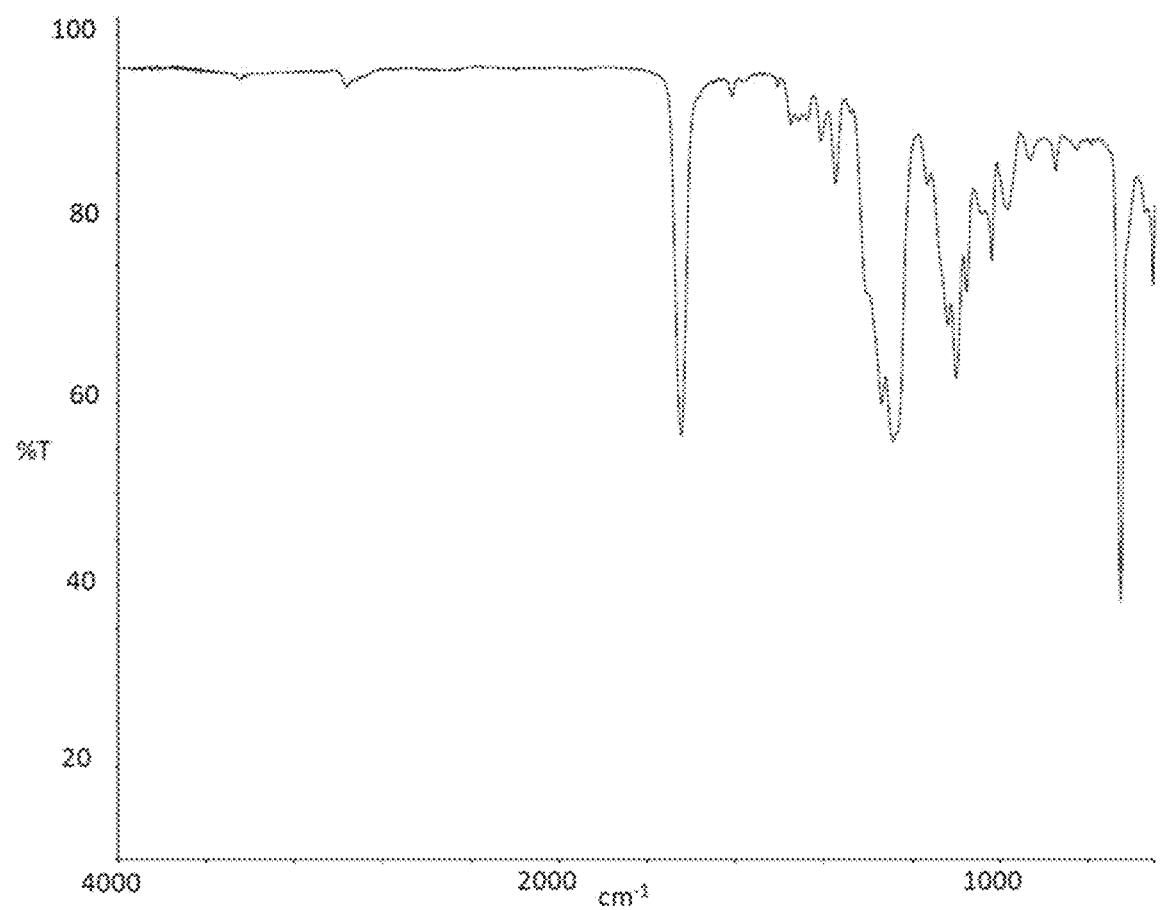

The FT-IR-spectra (Perkin Elmer Spektrum BX; ATR unit, FMIR unit, wavenumbers: 4000 cm-1 to 600 cm-1, resolution: 4 cm-1, number of scans: 16) are shown in FIGS. 8 and 9, with FIG. 8 being a measurement of a foil of the invention, and FIG. 9 a measurement of the Futamura, Natureflex NM foil. The foil of the invention (structure as per FIG. 2; 79.0 wt % cellulose (regenerated), 11 wt % glycerol, 6 wt % water, 3 wt % urea, 1 wt % aluminum) in FIG. 8 shows only bands which are typical of cellophane. The Natureflex NM foil in FIG. 9 shows additional bands which suggest a polyester-based coating.

Example 7

A further exemplary glitter was produced as in example 5, the pullulan coating having been replaced by a cellulose acetate coating. The solvent resistance obtained for this glitter was the same as for the glitter in example 5.

What is claimed is:

1. A glitter comprising a foil and an aluminum layer directly coating said foil and constituting a metal-coated foil, wherein the foil comprises at least 70 wt% of natural cellulose, based on the weight of the foil, said natural cellulose consist of unaltered glucose units.

2. The glitter as claimed in claim 1, wherein said foil and/or said aluminum layer is coated with a coating based on cellulose or modified cellulose, and/or based on polyurethane.

3. The glitter as claimed in claim 1, wherein said metal-coated foil has an optical density of more than 1.0.

4. The glitter as claimed in claim 1, wherein said foil has a thickness of 5 μm or more, and wherein the foil has a thickness of 50 μm or less.

5. The glitter as claimed in claim 1, wherein the foil has a transmissivity for light in the wavelength range from 380 to 780 nm of at least 70%.

6. A cosmetic product comprising a glitter as claimed in claim 1.

7. A coating material comprising a glitter as claimed in claim 1.

8. A plastic comprising a glitter as claimed in claim 1.

9. The glitter of claim 2, wherein the modified cellulose is based on cellulose nitrate, cellulose acetate butyrate, cellulose acetate propionate and/or cellulose acetate.

* * * * *